United States Patent
Lindsley et al.

(10) Patent No.: US 7,776,886 B2
(45) Date of Patent: Aug. 17, 2010

(54) CYCLOPROPYL PIPERIDINE GLYCINE TRANSPORTER INHIBITORS

(75) Inventors: Craig W. Lindsley, Schwenksville, PA (US); David D. Wisnoski, Quakertown, PA (US); Scott E. Wolkenberg, Jenkintown, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 256 days.

(21) Appl. No.: 11/664,190

(22) PCT Filed: Sep. 26, 2005

(86) PCT No.: PCT/US2005/034301

§ 371 (c)(1),
(2), (4) Date: Mar. 28, 2007

(87) PCT Pub. No.: WO2006/039221

PCT Pub. Date: Apr. 13, 2006

(65) Prior Publication Data

US 2008/0108663 A1 May 8, 2008

Related U.S. Application Data

(60) Provisional application No. 60/614,942, filed on Sep. 30, 2004.

(51) Int. Cl.
 A61K 31/445 (2006.01)
 C07D 211/96 (2006.01)
(52) U.S. Cl. .................... 514/331; 514/233; 546/184
(58) Field of Classification Search .................... None
 See application file for complete search history.

(56) References Cited

U.S. PATENT DOCUMENTS

| 6,303,637 | B1 | 10/2001 | Bao et al. | |
|---|---|---|---|---|
| 6,458,790 | B2 | 10/2002 | Palucki | |
| 7,071,213 | B2 | 7/2006 | Friary | |
| 2006/0276655 | A1 | 12/2006 | Blackaby et al. | |
| 2007/0105902 | A1* | 5/2007 | Lindsley et al. | 514/317 |
| 2007/0249606 | A1 | 10/2007 | Lindsley et al. | |
| 2007/0254880 | A1 | 11/2007 | Blackaby et al. | |
| 2008/0021010 | A1 | 1/2008 | Lindsley et al. | |
| 2008/0090796 | A1 | 4/2008 | Blackaby et al. | |

FOREIGN PATENT DOCUMENTS

| WO | WO 96/25397 | | 8/1996 |
|---|---|---|---|
| WO | WO 00/25786 | * | 5/2000 |
| WO | WO 02/062750 | | 8/2002 |
| WO | WO 03/042174 | * | 5/2003 |
| WO | 03/055478 | | 7/2003 |
| WO | WO 03/088908 | | 10/2003 |
| WO | WO 2005/046601 | | 5/2005 |
| WO | WO 2005/094514 | | 10/2005 |
| WO | WO 2005/107469 | | 11/2005 |
| WO | WO 2005/110983 | | 11/2005 |
| WO | WO 2006/067529 | | 6/2006 |
| WO | WO 2007/041025 | | 4/2007 |
| WO | WO 2007/053400 | | 5/2007 |

OTHER PUBLICATIONS

Rogers et al (Brain Res, 493:41-50, 1989).*
Brinker (Advances in Carbene Chemistry, vol. 3, 2001, pp. 20-21).*
Zhao et al (Bioorg Med Chem Lett 16:5968-5972, 2006).*
Lindsley et al (Chem Med Chem 1:807-811, 2006).*
Zhao et al (Bioorg Med Chem Lett 19:1488-1491, 2009).*
Thomson et al (Bioorg Med Chem Lett 19:2235-2239, 2009).*
Hovgaard et al (Pharm Res 12:387-392, 1995).*
Ulbrich et al (J Med Chem 37:953-959, 2002).*
Williams et al (Foye's Principles of Medicinal Chemistry, pp. 59-61, 2001).*
Patani et al (Chem Rev 96:3147-3176, 1996).*
Cockerham et al (Basic Environmental Toxicology, pp. 201-204, 1994).*
Wolkenberg, S.E., et. al., Discovery of GlyT1 Inhibitors with Improved Pharmacokinetic Properties, Bioorganic & Medicinal Chemistry Letters (2009), doi: 10.1016/j.bmcl.2009.01.015.
Copending U.S. Appl. No. 11/991,727, filed Sep. 25, 2006, U.S. National Stage Entry of PCT/GB06/036989, published as WO 2007/041025.
Copending U.S. Appl. No. 12/084,027, filed Oct. 27, 2006, U.S. National Stage Entry of PCT/GB06/041699, published as WO 2007/053400.
Copending U.S. Appl. No. 12/085,340, filed Nov. 23, 2006, U.S. National Stage Entry of PCT/GB06/050411, published as WO 2007/060484.
Copending U.S. Appl. No. 11/922,074, filed Jun. 13, 2006, U.S. National Stage Entry of PCT/GB06/002156, published as WO 2006/134341.
Supplementary Partial European Search Report for EP Application No. 05 80 1197.

\* cited by examiner

*Primary Examiner*—Brandon J Fetterolf
*Assistant Examiner*—Craig Ricci
(74) *Attorney, Agent, or Firm*—Gerard Devlin; Raynard Yuro

(57) ABSTRACT

The present invention is directed to cyclopropyl piperidine compounds that inhibit the glycine transporter GlyT1 and which are useful in the treatment of neurological and psychiatric disorders associated with glycinergic or glutamatergic neuro-transmission dysfunction and diseases in which the glycine transporter GlyT1 is involved.

13 Claims, No Drawings

CYCLOPROPYL PIPERIDINE GLYCINE TRANSPORTER INHIBITORS

CROSS REFERENCE TO RELATED APPLICATIONS

This application is a U.S. National Phase application under 35 U.S.C. 371 of PCT Application No. PCT/US2005/034301, filed Sep. 26, 2005, which claims priority under 35 U.S.C. 119 from U.S. Application No. 60/614,942, filed Sep. 30, 2004.

BACKGROUND OF THE INVENTION

Schizophrenia is a debilitating psychiatric disorder characterized by a combination of negative (blunted affect, withdrawal, anhedonia) and positive (paranoia, hallucinations, delusions) symptoms as well as marked cognitive deficits. While the etiology of schizophrenia is currently unknown, the disease appears to be produced by a complex interaction of biological, environmental, and genetic factors. Over 40 years ago it was found that phencyclidine (PCP) induces a psychotic state in humans that is very similar to that observed in schizophrenic patients. The finding that the main mode of action of PCP is that of a non-competitive antagonist of the N-methyl-D-aspartate (NMDA) subtype of ionotropic glutamate receptor stimulated a series of studies that have led to the development of the NMDA receptor hypofunction model of schizophrenia (Jentsch J D and Roth R H, 1999 Neuropsychopharmacology, 20:201).

Fast glutamatergic transmission in the mammalian central nervous system is primarily mediated by the excitatory amino acid glutamate acting on ionotropic glutamate receptors (iGluRs). ° The iGluRs are comprised of three major subclasses, including the α-amino-3-hydroxy-5-methyl-4-isoxazolepropionic acid (AMPA), kainate, and NMDA receptor subtypes (Hollmann M and Heinemann S, 1994, Annu. Rev. Neurosci. 17:31). These three subclasses are multimeric ligand-gated cation channels which open in response to glutamate binding to induce a depolarizing excitatory post synaptic current. Molecular cloning has revealed that the NMDA receptor family is composed of two primary subunits, NR1 and NR2. In addition a novel inhibitory subunit which is developmentally regulated termed NR3 has been recently described. A high degree of molecular diversity exists within each set of subunits. To date, only one NR1 subunit gene has been cloned; however, alternative splicing of the NR1 gene can produce eight different subunits. In contrast, 4 genes have been cloned for the NR2 subunit (NR2A, NR2B, NR2C, and NR2D), some of which exhibit alternative splicing (Hollmann M and Heinemann S, 1994, Annu. Rev. Neurosci. 17:31). These multiple subunits form heteromeric glutamate-gated ion channels. While the precise subunit stoichiometry of the naturally occurring receptor remains unknown, both the NR1 and NR2 subunits are required for the expression of functionally active receptor-channel complexes in mammalian expression systems. Activation of the NMDA receptor requires the binding of both glutamate and glycine (Johnson J W and Ascher P, 1987, Nature 325:529). Interestingly, the binding sites for these two co-agonists exist on separate subunits as determined by site-directed mutagenesis studies (Laube B, Hirai H, Sturgess M, Betz H and Kuhse J, 1997, Neuron 18:493). On the NR2A and NR2B subunits, a binding pocket for glutamate is formed by interactions between the N-terminus of the receptor and the extracellular loops. Analogous experiments have placed the glycine binding site in a homologous region of the NR1 subunit (Kuryatov A, Laube B, Betz H and Kuhse J, 1994, Neuron 12:1291). Depending on the actual subunit composition, glutamate and glycine activate the NMDA receptor with EC50 values in the high nanomolar to low micromolar range. In addition, the pore of the NMDA receptor is impermeable to magnesium. Under normal resting conditions, extracellular magnesium can bind to a site within the pore and produce a magnesium block of the channel. This magnesium block imparts a strong voltage dependence to the channel which allows the NMDA receptor to act as a coincidence detector requiring the binding of glutamate, glycine, and the occurrence of postsynaptic depolarization before conducting current. Of particular interest is the finding that the psychotomimetic drugs MK-801, PCP, and ketamine all act as open channel blockers of the NMDA receptor-channel by binding to a site that overlaps with the magnesium binding site. It is apparent that the rich diversity of NMDA receptor subunits and regulatory sites provides for a complex assortment of physiologically and pharmacologically distinct heteromeric receptors making the NMDA receptor an ideal target for the design of novel therapeutic compounds.

The NMDA receptor plays a critical role in a variety of neurophysiological phenomena, including but not limited to synaptic plasticity, cognition, attention and memory (Bliss T and Collingridge W, 1993, Nature 361:31; Morris R G M et al., 1986, Nature 319:774). Psychotomimetic drugs constitute a wide class of drugs including psychomotor stimulants (cocaine, amphetamine), hallucinogens (LSD), and NMDA receptor antagonists (PCP, ketamine). Of these, only the NMDA receptor antagonists appear to elicit a robust induction of the positive, negative, and cognitive symptoms of schizophrenia. Controlled studies of ketamine-induced psychosis in human subjects, as well as observations of symptoms from patients abusing PCP as a recreational drug, have produced a convincing list of similarities between NMDA receptor antagonist-induced psychosis and schizophrenia (Jentsch J D and Roth R H, 1999 Neuropsychopharmacology, 20:201). NMDA-receptor antagonists faithfully mimic the symptoms of schizophrenia to the extent that it is difficult to differentiate the two in the clinic. In addition, NMDA receptor antagonists can exacerbate the symptoms in schizophrenics, and can trigger the re-emergence of symptoms in stable patients. Finally, the finding that NMDA receptor co-agonists such as glycine, D-cycloserine, and D-serine produce benefits in schizophrenic patients implicates NMDA receptor hypofunction in this disorder, and indicate that increasing NMDA receptor activation may provide a therapeutic benefit (Leiderman E et al., 1996, Biol. Psychiatry 39:213, Javitt D C et al., 1994, Am. J. Psychiatry 151:1234, Heresco-Levy U, 2000, Int. J. Neuropsychopharmacol. 3:243, Tsai G et al., 1998, Biol. Psychiatry 44:1081). A large number of studies in animal models lend support to the NMDA hypofunction hypothesis of schizophrenia. Recent generation of a mutant mouse expressing only 5% of normal levels of the NMDA NR1 subunit have shown that this decrease in functional NMDA receptors induces a state very similar to that observed in other animal models of schizophrenia (Mohn A R et al., 1999, Cell 98:427). Besides schizophrenia, dysfunction of glutamatergic pathways has been implicated in a number of disease states in the human central nervous system (CNS) including but not limited to cognitive deficits, dementia, Parkinson disease, Alzheimer disease and bipolar disorder.

NMDA receptor function can be modulated by altering the availability of the co-agonist glycine. This approach has the critical advantage of maintaining activity-dependent activation of the NMDA receptor because an increase in the synaptic concentration of glycine will not produce an activation of NMDA receptors in the absence of glutamate. Since synaptic glutamate levels are tightly maintained by high affinity transport mechanisms, an increased activation of the glycine site will only enhance the NMDA component of activated synapses. Clinical trials in which high doses of glycine were administered orally as an add-on to standard neuroleptic therapy showed an improvement of the symptoms of schizophrenia patients (Javitt et al. Int. J. Neuropsychopharmacol. (2001) 4: 385-391). One way to increase synaptic glycine levels without administering exogenous glycine is to inhibit its removal from the synapse. Evidence that this approach would be useful in treating schizophrenia comes from a double-blind placebo controlled study in which sarcosine was administered to patients suffering from schizophrenia, but who were poorly responsive to antipsychotic drugs. A beneficial effect was observed on positive, negative and cognitive symptoms, indicating that inhibition of glycine re-uptake is a reasonable approach to the treatment of schizophrenia.

Two specific glycine transporters, GlyT1 and GlyT2 have been identified and shown to belong to the Na+/Cl− dependent family of neurotransmitter transporters which includes taurine, γ-amino-butyric acid (GABA), proline, monoamines and orphan transporters (Smith K E et al., 1992, Neuron 8:927; Borowsky B et al., 1993, Neuron 10:851; Liu Q R et al., 1993, J. Biol. Chem. 268:22802; Kim K M et al., 1994, Mol. Pharmacol. 45:608; Morrow J A et al., 1998, FEBS Lett. 439:334; Nelson N, 1998, J. Neurochem. 71:1785). GlyT1 and GlyT2 have been isolated from different species and shown to have only 50% identity at the amino acid level. They also have a different pattern of expression in mammalian central nervous system with GlyT2 being expressed in spinal cord, brainstem and cerebellum and GlyT1 present in these regions as well as forebrain areas such as cortex, hippocampus, septum and thalamus (Smith K E et al., 1992, Neuron 8:927; Borowsky B et al., 1993, Neuron 10:851; Liu Q R et al., 1993, J. Biol. Chem. 268:22802). At the cellular level, GlyT2 has been reported to be expressed by glycinergic nerve endings in rat spinal cord whereas GlyT1 appears to be preferentially expressed by glial cells (Zafra F et al., 1995, J. Neurosci. 15:3952). These expression studies have led to the conclusion that GlyT2 is predominantly responsible for glycine uptake at glycinergic synapses whereas GlyT1 is involved in monitoring glycine concentration in the vicinity of NMDA receptor expressing synapses. Recent functional studies in rat have shown that blockade of GlyT1 with the potent inhibitor (N-[3-(4'-fluorophenyl)-3-(4'-phenylphenoxy)propyl])sarcosine (NFPS) potentiates NMDA receptor activity and NMDA receptor-dependent long-term potentiation in rat (Bergeron R et al., 1998, PNAS USA 95:15730; Kinney G et al., 2003, J. Neurosci. 23:7586). Furthermore, NFPS has been reported to enhance pre-pulse inhibition in mice, a measure of sensory gating that is known to be deficient in schizophrenia patients (Kinney G et al., 2003, J. Neurosci. 23:7586). These physiological effects of GlyT1 in forebrain regions together with clinical reports showing the beneficial effects of GlyT1 inhibitor sarcosine in improving symptoms in schizophrenia patients (Tsai and Coyle WO99/52519) indicate that selective GlyT1 uptake inhibitors represent a new class of antipsychotic drugs.

SUMMARY OF THE INVENTION

The present invention is directed to compounds that inhibit the glycine transporter GlyT1 and which are useful in the treatment of neurological and psychiatric disorders associated with glutamatergic neurotransmission dysfunction and diseases in which the glycine transporter GlyT1 is involved.

DETAILED DESCRIPTION OF THE INVENTION

The present invention is directed to compounds of the formula I:

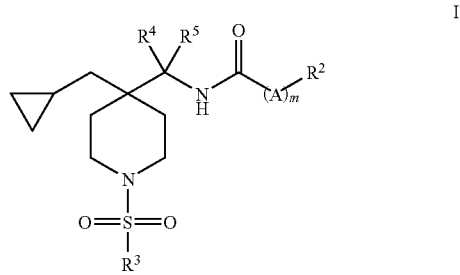

wherein:

$R^2$ is selected from the group consisting of:
 (1) phenyl, which is substituted with $R^{2a}$, $R^{2b}$ and $R^{2c}$,
 (2) heterocycle, which is substituted with $R^{2a}$, $R^{2b}$ and $R^{2c}$,
 (3) $C_{1-8}$alkyl, which is unsubstituted or substituted with 1-6 halogen, hydroxy, —$NR^{10}R^{11}$, phenyl or heterocycle, where the phenyl or heterocycle is substituted with $R^{2a}$, $R^{2b}$ and $R^{2c}$,
 (4) $C_{3-6}$cycloalkyl, which is unsubstituted or substituted with 1-6 halogen, hydroxy or —$NR^{10}R^{11}$,
  wherein $R^{10}$ and $R^{11}$ are independently selected from:
  (a) hydrogen,
  (b) —$C_{1-6}$alkyl, which is unsubstituted or substituted with hydroxy, 1-6 fluoro or —$NR^{12}R^{13}$, where $R^{12}$ and $R^{13}$ are independently selected from hydrogen and —$C_{1-6}$alkyl,
  (c) —$C_{3-6}$cycloalkyl, which is unsubstituted or substituted with hydroxy, 1-6 fluoro or —$NR^{12}R^{13}$,
  (d) benzyl,
  (e) phenyl, and
 (5) —$C_{1-6}$alkyl-($C_{3-6}$cycloalkyl), which is unsubstituted or substituted with 1-6 halogen, hydroxy or —$NR^{10}R^{11}$;

$R^{2a}$, $R^{2b}$ and $R^{2c}$ are independently selected from the group consisting of:
 (1) hydrogen,
 (2) halogen,
 (3) —$C_{1-6}$alkyl, which is unsubstituted or substituted with:
  (a) 1-6 halogen,
  (b) phenyl,
  (c) $C_{3-6}$cycloalkyl, or
  (d) —$NR^{10}R^{11}$,
 (4) —O—$C_{1-6}$alkyl, which is unsubstituted or substituted with 1-6 halogen,
 (5) hydroxy,
 (6) —$SCF_3$,
 (7) —$SCHF_2$,
 (8) —$SCH_3$,
 (9) —$CO_2R^9$,
  wherein $R^9$ is independently selected from:
  (a) hydrogen,
  (b) —$C_{1-6}$alkyl, which is unsubstituted or substituted with 1-6 fluoro,
  (c) benzyl, and
  (d) phenyl,

(10) —CN,
(11) —SO$_2$R$^9$,
(12) —SO$_2$—NR$^{10}$R$^{11}$,
(13) —NR$^{10}$R$^{11}$,
(14) —CONR$^{10}$R$^{11}$, and
(15) —NO$_2$;

R$^3$ is C$_{1-6}$alkyl or C$_{3-6}$cycloalkyl, which are independently unsubstituted or substituted with 1-6 halogen, hydroxyl, —NR$^{10}$R$^{11}$, or heterocycle, which is substituted with R$^{2a}$, R$^{2b}$ and R$^{2c}$;

R$^4$ and R$^5$ are independently selected from the group consisting of:
(1) hydrogen, and
(2) C$_{1-6}$alkyl, which is unsubstituted or substituted with halogen or hydroxyl, or R$^4$ and R$^5$ taken together form a C$_{3-6}$cycloalkyl ring;

A is selected from the group consisting of:
(1) —O—, and
(2) —NR$^{10}$—;

m is zero or one, whereby when m is zero R$^2$ is attached directly to the carbonyl;

and pharmaceutically acceptable salts thereof and individual enantiomers and diastereomers thereof.

An embodiment of the present invention includes compounds of the formula Ia:

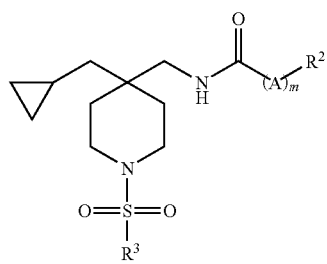

Ia wherein R$^2$, R$^3$, A and m are defined herein;

or a pharmaceutically acceptable salt thereof or an individual enantiomer or diastereomer thereof.

An embodiment of the present invention includes compounds of the formula Ib:

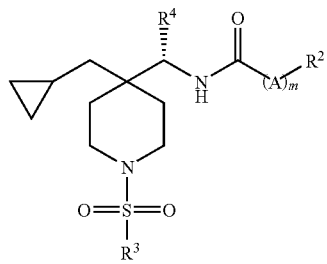

Ib wherein R$^4$ is C$_{1-6}$alkyl, and R$^2$, R$^3$, A and m are defined herein;

or a pharmaceutically acceptable salt thereof or an individual enantiomer or diastereomer thereof.

An embodiment of the present invention includes compounds wherein R$^4$ is C$_{1-3}$alkyl and R$^5$ is hydrogen or C$_{1-3}$alkyl.

Within this embodiment, the present invention includes compounds wherein R$^4$ is C$_{1-3}$alkyl in the (S) configuration and R$^5$ is hydrogen.

Also within this embodiment, the present invention includes compounds wherein R$^4$ is methyl and R$^5$ is hydrogen.

Also within this embodiment, the present invention includes compounds wherein R$^4$ is methyl and R$^5$ is methyl.

Also within this embodiment, the present invention includes compounds wherein R$^4$ is hydrogen and R$^5$ is hydrogen.

An embodiment of the present invention includes compounds wherein m is zero.

Within this embodiment, the present invention includes compounds of the formula Ic:

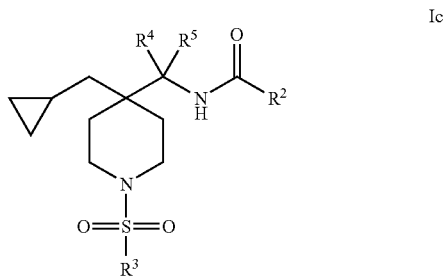

Ic wherein R$^2$, R$^3$, R$^4$ and R$^5$ are defined herein;

or a pharmaceutically acceptable salt thereof or an individual enantiomer or diastereomer thereof.

Further within this embodiment, the present invention includes compounds wherein R$^2$ is selected from the group consisting of:
(1) phenyl, which is substituted with R$^{2a}$, R$^{2b}$ and R$^{2c}$,
(2) furanyl, which is substituted with R$^{2a}$, R$^{2b}$ and R$^{2c}$,
(3) C$_{1-8}$alkyl, which is unsubstituted or substituted with 1-6 halogen, phenyl or —NR$^{10}$R$^{11}$, where the phenyl is substituted with R$^{2a}$, R$^{2b}$ and R$^{2c}$,
(4) C$_{3-6}$cycloalkyl, which is unsubstituted or substituted with 1-6 halogen, hydroxy or —NR$^{10}$R$^{11}$, and R$^{2a}$, R$^{2b}$ and R$^{2c}$ are independently selected from the group consisting of:
(1) hydrogen,
(2) halogen,
(3) —C$_{1-6}$alkyl,
(4) —)—C$_{1-6}$alkyl,
(5) —CF$_3$,
(6) —OCF$_3$,
(7) —OCHF$_2$,
(8) —SCF$_3$,
(9) —SCHF$_2$, and
(10) —NH$_2$.

Also further within this embodiment, the present invention includes compounds wherein R$^2$ is phenyl or furanyl and R$^{2a}$, R$^{2b}$ and R$^{2c}$ are independently selected from the group consisting of:
(1) hydrogen,
(2) halogen,
(3) —C$_{1-6}$alkyl,
(4) —O—C$_{1-6}$alkyl, (5) —CF$_3$,
(6) —OCF$_3$,
(7) —OCHF$_2$,
(8) —SCF$_3$,
(9) —SCHF$_2$, and
(10) —NH$_2$.

Also further within this embodiment, the present invention includes compounds wherein R$^2$ is phenyl and R$^{2a}$, R$^{2b}$ and R$^{2c}$ are independently selected from the group consisting of:

(1) hydrogen,
(2) fluoro,
(3) chloro,
(4) bromo,
(5) —OCH$_3$,
(6) —CF$_3$,
(7) —NH$_2$.

Also further within this embodiment, the present invention is directed to compounds wherein R$^2$ is phenyl and R$^{2a}$, R$^{2b}$ and R$^{2c}$ are independently selected from the group consisting of:

(1) hydrogen,
(2) fluoro,
(3) chloro, and
(4) bromo.

Also further within this embodiment, the present invention is directed to compounds wherein R$^2$ is phenyl and R$^{2a}$, R$^{2b}$ and R$^{2c}$ are independently selected from the group consisting of:

(1) hydrogen,
(2) fluoro, and
(3) chloro.

Also further within this embodiment, the present invention is directed to compounds wherein R$^2$ is phenyl and R$^{2a}$, R$^{2b}$ and R$^{2c}$ are independently selected from the group consisting of:

(1) hydrogen, and
(2) fluoro.

Also further within this embodiment, the present invention is directed to compounds wherein R$^2$ is phenyl and R$^{2a}$, R$^{2b}$ and R$^{2c}$ are independently selected from the group consisting of:

(1) hydrogen, and
(2) chloro.

Also further within this embodiment, the present invention is directed to compounds wherein R$^2$ is selected from the group consisting of:

(1) 2,3-difluorophenyl,
(2) 2,4-difluorophenyl,
(3) 2,4-dichlorophenyl,
(4) 2-chloro-4-fluorophenyl,
(5) 2-chloro-6-fluorophenyl, and
(6) 2-chloro-4,6-difluorophenyl, Within this embodiment the present invention includes compounds of the formula Id:

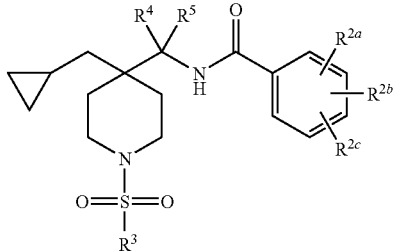

Id wherein R$^{2a}$, R$^{2b}$, R$^{2c}$, R$^3$, R$^4$ and R$^5$ are defined herein;
and pharmaceutically acceptable salts thereof and individual enantiomers and diastereomers thereof.

Within this embodiment, the present invention includes compounds of the formula Id'

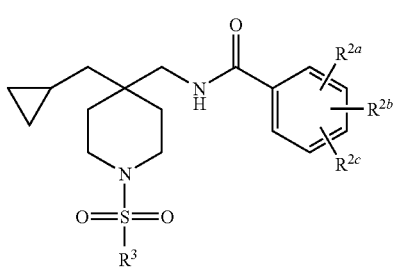

Id' wherein R$^{2a}$, R$^{2b}$, R$^{2c}$ and R$^3$ are defined herein;
and pharmaceutically acceptable salts thereof and individual enantiomers and diastereomers thereof.

Also within this embodiment, the present invention includes compounds of the formula Id":

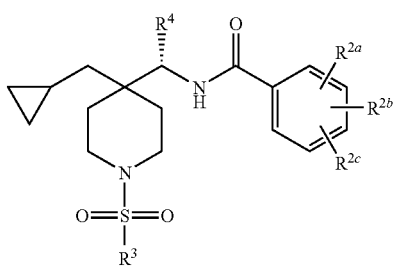

Id"

wherein R$^{2a}$, R$^{2b}$, R$^{2c}$, R$^3$ and R$^4$ are defined herein;
and pharmaceutically acceptable salts thereof and individual enantiomers and diastereomers thereof.

An embodiment of the present invention includes compounds wherein R$^3$ is C$_{1-6}$alkyl.

Within this embodiment, the present invention includes compounds wherein R$^3$ is —CH$_2$CH$_3$.

Within this embodiment, the present invention includes compounds wherein R$^3$ is —CH$_2$CF$_3$.

Within this embodiment, the present invention includes compounds wherein R$^3$ is —(CH$_2$)$_2$CH$_3$.

Within this embodiment, the present invention includes compounds wherein R$^3$ is —CH(CH$_3$)$_2$.

Also within this embodiment, the present invention includes compounds wherein $R^3$ is cyclopropyl.

Specific embodiments of the present invention include a compound which is selected from the group consisting of the subject compounds of the Examples herein and pharmaceutically acceptable salts thereof and individual enantiomers and diastereomers thereof.

The compounds of the present invention may contain one or more chiral centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without preferred stereochemistry.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As appreciated by those of skill in the art, halo or halogen as used herein are intended to include fluoro, chloro, bromo and iodo. Similarly, $C_{1-6}$ as in $C_{1-6}$alkyl is defined to identify the group as having 1, 2, 3, 4, 5 or 6 carbons in a linear or branched arrangement, such that $C_{1-8}$alkyl specifically includes methyl, ethyl, n-propyl, iso-propyl, n-butyl, iso-butyl, tert-butyl, pentyl, hexyl, heptyl and octyl. A group which is designated as being independently substituted with substituents may be independently substituted with multiple numbers of such substituents. The term "heterocycle" as used herein includes both unsaturated and saturated heterocyclic moieties, wherein the unsaturated heterocyclic moieties (i.e. "heteroaryl") include benzoimidazolyl, benzimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolinyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, tetrahydrothienyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, and methylenedioxybenzoyl, and N-oxides thereof. In embodiments of the present invention, heterocycle is an unsaturated heterocyclic moiety ("heteroaryl") which is pyridyl or pyrimidyl or a saturated heterocyclic moiety which is piperidine or azetidine.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of inhibiting the glycine transporter GlyT1 activity in a patient such as a mammal in need of such inhibition comprising the administration of an effective amount of the compound. The present invention is directed to the use of the compounds disclosed herein as inhibitors of the glycine transporter GlyT1 activity.

In addition to primates, especially humans, a variety of other mammals can be treated according to the method of the present invention.

The present invention is further directed to a method for the manufacture of a medicament for inhibiting glycine transporter GlyT1 activity in humans and animals comprising combining a compound of the present invention with a pharmaceutical carrier or diluent.

The subject treated in the present methods is generally a mammal, preferably a human being, male or female, in whom inhibition of glycine transporter GlyT1 activity is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy to retard the progression or reduce the risk of the noted conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibiting the glycine transporter activity, in particular GlyT1 activity, may be demonstrated by methodology known in the art. Human placental choriocarcinoma cells (JAR cells (ATCC No. HTB-144)) endogenously expressing GlyT1 were cultured in 96-well Cytostar scintillating microplates (Amershaam Biosciences) in RPMI 1640 medium containing 10% fetal calf serum in the presence of penicillin (100 micrograms/milliliter) and streptomycin (100 micrograms/milliliter). Cells were grown at 37° C. in a humidified atmosphere of 5% CO2 for 40-48 hours before the assay. Culture medium was removed from the Cytostar plate, and JAR cells were incubated with 30 microliters of TB 1A buffer (120 mM NaCl, 2 mM KCl, 1 mM $CaCl_2$, 1 mM $MgCl_2$, 10 mM HEPES, 5 mM L-alanine, pH 7.5 adjusted with Tris base) with or without the compounds of the present invention for 1 minute. Then 30 microliters of [$^{14}$C]-glycine diluted with TBIA was added to each well to give a final concentration of 10 micromolar. After incubation at room temperature for 3 hours, the Cytostar scintillating microplates were sealed and counted on a Top Count scintillation counter (Packard). Non-specific uptake of [$^{14}$C]-glycine was determined in the presence of 10 mM unlabeled glycine. [$^{14}$C] taurine uptake experiments were performed according to the same protocol except that 10 mM unlabeled taurine was used to determine non-specific uptake. To determine potencies, a range of concentrations of the compounds of the present invention was added to the cells, followed by the fixed concentration of [$^{14}$C]glycine. The concentration of the present compound that inhibited half of the specific uptake of [$^{14}$C] glycine ($IC_{50}$ value) was determined from the assay data by non-linear curve fitting.

In particular, the compounds of the following examples had activity in inhibiting specific uptake of [$^{14}$C]glycine in the aforementioned assay, generally with an $IC_{50}$ value of less than about 10 micromolar. Preferred compounds within the present invention had activity in inhibiting specific uptake of [$^{14}$C]glycine in the aforementioned assay with an $IC_{50}$ value of less than about 1 micromolar. These compounds were selective for [$^{14}$C]glycine uptake (by GlyT1 in the JAR cells) compared to [$^{14}$C]taurine uptake (by the taurine transporter TauT in the JAR cells). Such a result is indicative of the intrinsic activity of the compounds in use as inhibitors of GlyT1 transporter activity.

The NMDA receptor is central to a wide range of CNS processes, and plays a role in a variety of disease states in humans or other species. The action of GlyT1 transporters affects the local concentration of glycine around NMDA receptors. Selective GlyT1 inhibitors slow the removal of glycine from the synapse, causing the level of synaptic glycine to rise. This in turn increases the occupancy of the glycine binding site on the NMDA receptor, which increases activation of the NMDA receptor following glutamate release from the presynaptic terminal. Because a certain amount of glycine is needed for the efficient functioning of NMDA receptors, any change to that local concentration can affect NMDA-mediated neurotransmission. Changes in NMDA-mediated neurotransmission have been implicated in certain neuropsychiatric disorders such as dementia, depression and psychoses, for example schizophrenia, and learning and memory disorders, for example attention deficit disorders and autism.

The compounds of the present invention have utility in treating a variety of neurological and psychiatric disorders associated with glutamatergic neurotransmission dysfunction, including one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa and compulsive eating disorders; bipolar disorders, mood disorders including depressive disorders; depression including unipolar depression, seasonal depression and post-partum depression, premenstrual syndrome (PMS) and premenstrual dysphoric disorder (PDD), mood disorders due to a general medical condition, and substance-induced mood disorders; learning disorders, pervasive developmental disorder including autistic disorder, attention disorders including attention-deficit hyperactivity disorder (ADHD) and conduct disorder; NMDA receptor-related disorders such as autism, depression, benign forgetfulness, childhood learning disorders and closed head injury; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors; dyskinesias [including tremor (such as rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia)]; urinary incontinence; neuronal damage including ocular damage, retinopathy or macular degeneration of the eye, tinnitus, hearing impairment and loss, and brain edema; emesis; and sleep disorders including insomnia and narcolepsy.

Of the disorders above, the treatment of schizophrenia, bipolar disorder, depression including unipolar depression, seasonal depression and post-partum depression, premenstrual syndrome (PMS) and premenstrual dysphoric disorder (PDD), learning disorders, pervasive developmental disorder including autistic disorder, attention disorders including Attention-Deficit/Hyperactivity Disorder, autism, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

In a specific embodiment, the present invention provides a method for treating cognitive disorders, comprising: administering to a patient in need thereof an effective amount of a compound of the present invention. Particular cognitive disorders are dementia, delirium, amnestic disorders and age-related cognitive decline. At present, the text revision of the fourth edition of the Diagnostic and Statistical Manual of Mental Disorders (DSM-IV-TR) (2000, American Psychiatric Association, Washington D.C.) provides a diagnostic tool that includes cognitive disorders including dementia, delirium, amnestic disorders and age-related cognitive decline. As used herein, the term "cognitive disorders" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "cognitive disorders" is intended to include like disorders that are described in other diagnostic sources.

In another specific embodiment, the present invention provides a method for treating anxiety disorders, comprising: administering to a patient in need thereof an effective amount of a compound of the present invention. Particular anxiety disorders are generalized anxiety disorder, obsessive-compulsive disorder and panic attack. At present, the text revision of the fourth edition of the Diagnostic and Statistical Manual of Mental Disorders (DSM-IV-TR) (2000, American Psychiatric Association, Washington D.C.) provides a diagnostic tool that includes anxiety disorders are generalized anxiety disorder, obsessive-compulsive disorder and panic attack. As used herein, the term "anxiety disorders" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "anxiety disorders" is intended to include like disorders that are described in other diagnostic sources.

In another specific embodiment, the present invention provides a method for treating schizophrenia or psychosis comprising: administering to a patient in need thereof an effective amount of a compound of the present invention. Particular schizophrenia or psychosis pathologies are paranoid, disorganized, catatonic or undifferentiated schizophrenia and substance-induced psychotic disorder. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

In another specific embodiment, the present invention provides a method for treating substance-related disorders and addictive behaviors, comprising: administering to a patient in need thereof an effective amount of a compound of the present invention. Particular substance-related disorders and addictive behaviors are persisting dementia, persisting amnestic disorder, psychotic disorder or anxiety disorder induced by substance abuse; and tolerance of, dependence on or withdrawal from substances of abuse. At present, the text revision of the fourth edition of the Diagnostic and Statistical Manual of Mental Disorders (DSM-IV-TR) (2000, American Psychiatric Association, Washington D.C.) provides a diagnostic tool that includes persisting dementia, persisting amnestic disorder, psychotic disorder or anxiety disorder induced by substance abuse; and tolerance of, dependence on or withdrawal from substances of abuse. As used herein, the term "substance-related disorders and addictive behaviors" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "substance-related disorders and addictive behaviors" is intended to include like disorders that are described in other diagnostic sources.

In another specific embodiment, the present invention provides a method for treating pain, comprising: administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In another specific embodiment, the present invention provides a method for treating obesity or eating disorders associated with excessive food intake and complications associated therewith, comprising: administering to a patient in need thereof an effective amount of a compound of the present invention. At present, obesity is included in the tenth edition of the International Classification of Diseases and Related Health Problems (ICD-10) (1992 World Health Organization) as a general medical condition. The text revision of the fourth edition of the Diagnostic and Statistical Manual of Mental Disorders (DSM-IV-TR) (2000, American Psychiatric Association, Washington D.C.) provides a diagnostic tool that includes obesity in the presence of psychological factors affecting medical condition. As used herein, the term "obesity or eating disorders associated with excessive food intake" includes treatment of those medical conditions and disorders described in ICD-10 and DSM-IV-TR. The skilled artisan will recognize that there are alternative nomenclatures, nosologies and classification systems for general medical conditions, and that these systems evolve with medical and scientific progress. Thus the term "obesity or eating disorders associated with excessive food intake" is intended to include like conditions and disorders that are described in other diagnostic sources.

The subject compounds are further useful in a method for the prevention, treatment, control, amelioration, or reducation of risk of the diseases, disorders and conditions noted herein.

The subject compounds are further useful in a method for the prevention, treatment, control, amelioration, or reduction of risk of the aforementioned diseases, disorders and conditions in combination with other agents, including an inhibitor of glycine transporter GlyT1 activity.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is preferred. However, the combination therapy may also includes therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alenternol, aripiprazole, amisulpride, benzhexol, bromocriptine, biperiden, chlorpromazine, chlorprothicene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetraberiazine, trihexyphenidyl, thioridazine, thiothixene, trifluoperazine or ziprasidone.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, $^5$-$HT_{1A}$ agonists or antagonists, especially $^5$-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art.

In the treatment of conditions which require inhibition of glycine transporter GlyT1 activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100) mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15. 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day. This dosage regimen may be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Abbreviations used in the description of the chemistry and in the Examples that follow are: DCM dichloromethane; KHMDS potassium bis(trimethylsilyl)amide; EDCI 1-[3-(dimethyl-amino)propyl]-3-ethylcarbodiimide hydrochloride; EtOAc ethyl acetate; Ra—Ni Raney Nickel; HOBt hydroxybenzotriazole; THF tetrahydrofuran; MeOH methanol; DIEA diisopropylethylamine.

Several methods for preparing the compounds of this invention are illustrated in the following Schemes and Examples. Starting materials and the requisite intermediates are in some cases commercially available, or can be prepared according to literature procedures or as illustrated herein.

The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

REACTION SCHEME I

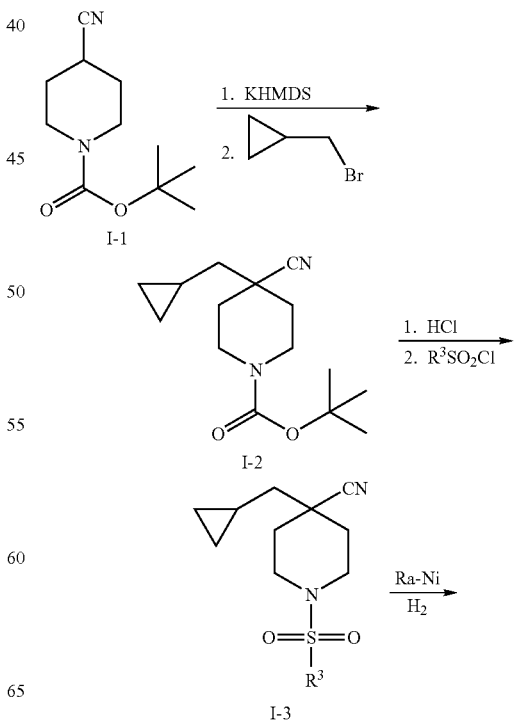

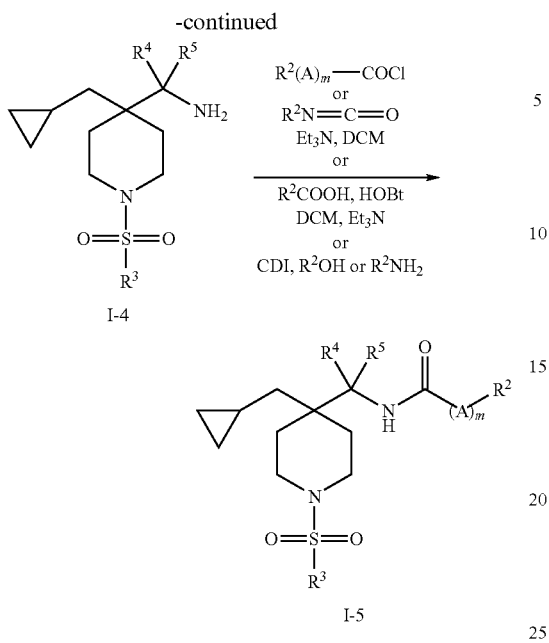

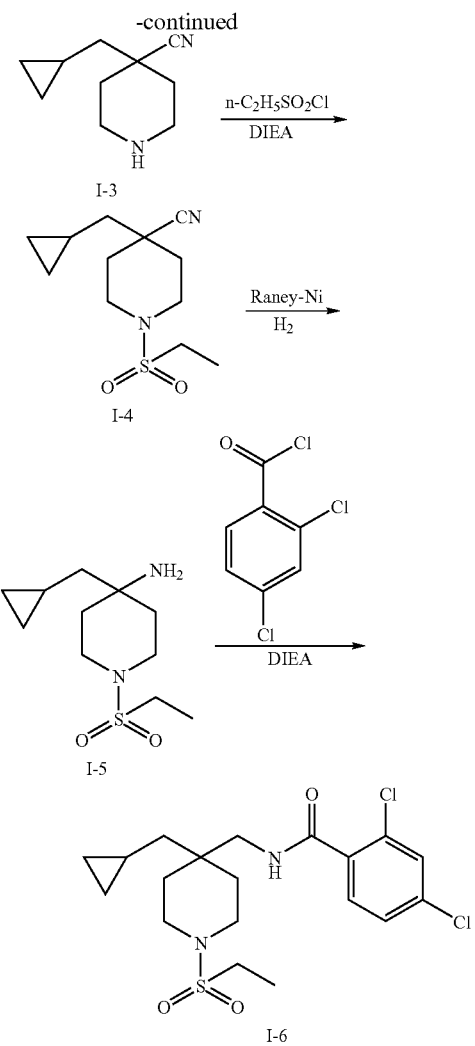

As illustrated in general Reaction Scheme I for the compounds of the present invention wherein $R^4$ is hydrogen and $R^5$ is hydrogen, a suitably substituted 4-cyanopiperidine is deprotonated employing KHMDS, followed by a nucleophilic aromatic substitution reaction with (bromomethyl)cyclopropane to provide I-2. Exposure of this material to HCl removes the Boc protecting group to afford the free amine which is treated with a sulfonyl chloride under standard reaction conditions to provide the corresponding sulfonamide. Hydrogenation employing Ra—Ni under a hydrogen atmosphere provides the corresponding amine, which is acylated under standard reactions conditions to deliver the final material. In this instance, the sulfonyl chlorides, acid chlorides and carboxylic acids employed were commercially available, as were the starting 4-cyanopiperidines.

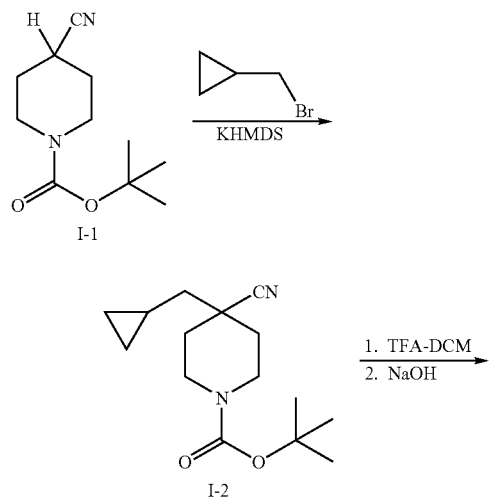

SCHEME 1 tert-Butyl 4-cyano-4-(cyclopropylmethyl)piperidine-1-carboxylate (I-2)

A solution of tert-butyl 4-cyanopiperidine-1-carboxylate I-1 (1.0 g, 4.8 mmol) in THF (20 mL) at room temperature was treated with KHMDS (9.6 mL of a 1.0 M solution in TBF, 9.6 mmol). After 30 min, (bromomethyl)cyclopropane (0.47 mL, 4.8 mmol) was added dropwise and the mixture was stirred until LCMS indicated the reaction was complete. The reaction mixture was poured into saturated aqueous $NH_4Cl$ (50 nil) and extracted with EtOAc (3×50 mL), and the combined organic extracts were dried ($Na_2SO_4$) and concentrated under reduced pressure to afford tert-butyl 4-cyano-4-(cyclopropyl-methyl)piperidine-1-carboxylate (I-2, M+H$^+$=265.2). This material was used in subsequent reactions without further purification.

4-(Cyclopropylmethyl)piperidine-4-carbonitrile hydrochloride (I-3)

A sample of tert-butyl 4-cyano-4-(cyclopropylmethyl)piperidine-1-carboxylate (I-2, 3.6 g, 13.6 mmol) was treated with HCl (40 mL of a 4.0 M solution in dioxane) and stirred at room temperature for 2 h before being concentrated under reduced pressure to afford 4-(cyclopropylmethyl)-piperidine-4-carbonitrile hydrochloride (I-3, M+H$^+$=165.1) which was used without further purification.

4-(Cyclopropylmethyl)-1-(ethylsulfonyl)piperidine-4-carbonitrile (I-4)

A suspension of 4-(cyclopropylmethyl)piperidine-4-carbonitrile hydrochloride (I-3, 2.5 g, 12.5 mmol) in $CH_2Cl_2$ (130 mL) at 0° C. was treated with i-$Pr_2$NEt (8.7 mL, 50 mmol) and $EtSO_2Cl$ (1.8 mL, 18.7 mmol) dropwise. After 2 h, the reaction was quenched with the addition of 1 M aqueous NaOH (40 mL) and stirred 18 h before being extracted with $CH_2Cl_2$ (3×50 mL). The combined organic extracts were dried ($Na_2SO_4$) and concentrated under reduced pressure to afford 4-(cyclopropylmethyl)-1-(ethylsulfonyl)piperidine-4-carbonitrile (I-4, M+H$^+$=256.1) as an off-white amorphous solid. This material was used in subsequent reactions without further purification.

1-[4-(Cyclopropylmethyl)-1-(ethylsulfonyl)piperidin-4-yl]methanamine (I-5)

A solution of 4-(cyclopropylmethyl)-1-(ethylsulfonyl)piperidine-4-carbonitrile (I-4, 3.1 mg, 11.1 mmol) in 2 M $NH_3$/MeOH (50 mL) was treated with excess Raney Ni and agitated under an atmosphere of $H_2$ (40 psi) in a Parr apparatus. After 5 h, the reaction was filtered through Celite (MeOH wash) and concentrated under reduced pressure to afford 1-[4-(cyclopropylmethyl)-1-(ethylsulfonyl)-piperidin-4-yl]methanamine (I-5, M+H$^+$=261.2) as a yellow oil. This material was used in subsequent reactions without further purification.

2,4-Dichloro-N-{[4-(cyclopropylmethyl)-1-(ethylsulfonyl)piperidin-4-yl]methyl}benzamide (I-6)

A solution of 1-[4-(cyclopropylmethyl)-1-(ethylsulfonyl)piperidin-4-yl]methanamine (I-5, 250 mg, 1.0 mmol) in $CH_2Cl_2$ (10 mL) at 0° C. was treated with i-$Pr_2$NEt (1 mL, 5.7 mmol), 2,4-dichlorobenzoyl chloride (200 µL, 1.43 mmol), and stirred for 15 min before being warmed to room temperature. After 1 h, the reaction was quenched with the addition of 1 M aqueous NaOH (10 mL) and stirred 1 h before being extracted with $CH_2Cl_2$ (3×20 mL). The combined organic extracts were dried ($Na_2SO_4$), concentrated under reduced pressure, and purified by reverse phase HPLC to afford 2,4-dichloro-N-{[4-(cyclopropylmethyl)-1-(ethylsulfonyl)piperidin-4-yl]methyl}benzamide (I-6) as an off-white amorphous solid. Analytical LCMS: single peak (214 nm), 3.328 min. $^1$H NMR (CDCl$_3$, 300 MHz) δ 7.64 (d, J=8.4 Hz, 1 H), 7.46 (s, 1H), 7.35 (d, J=8.4 Hz, 1H), 6.39 (t, J=8 Hz, 1H), 3.63 (d, J=6.3 Hz, 2H), 3.41 (m, 2H), 3.35 (m, 2H), 2.98 (q, J=7.2 Hz, 1H), 1.68 (m, 5H), 1.39 (m, 5H), 0.68 (m, 1H), 0.56 (d, J=8 Hz, 1H). HRMS m/z 433.1091 ($C_{19}H_{26}Cl_2N_2O_3S$+H$^+$ requires 433.1091).

The compounds in Table 1 were synthesized as shown in Reaction Scheme I, but substituting the appropriately substituted sulfonyl chloride and/or acid chloride/carboxylic acid as described in the Schemes and the foregoing examples. The requisite starting materials were commercially available, described in the literature or readily synthesized by one skilled in the art of organic synthesis without undue experimentation.

TABLE 1

| Compound | Nomenclature | MS M + 1 |
|---|---|---|
| 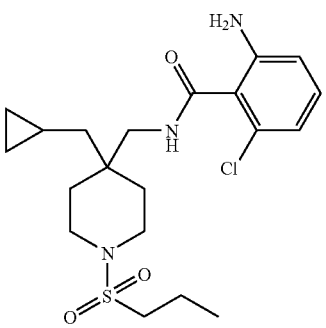 | 2-amino-6-chloro-N-{[4-(cyclopropylmethyl)-1-(propylsulfonyl)piperidin-4-yl]methyl}benzamide | 428.1 |
| 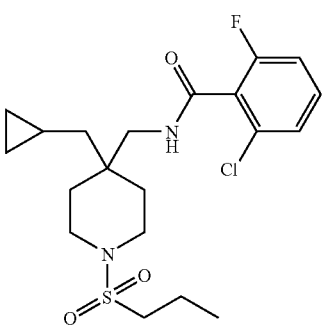 | 2-chloro-N-{[4-(cyclopropylmethyl)-1-(propylsulfonyl)piperidin-4-yl]methyl}-6-fluorobenzamide | 431.1 |

TABLE 1-continued

| Compound | Nomenclature | MS M + 1 |
|---|---|---|
| | 2-chloro-N-{[4-(cyclopropylmethyl)-1-(ethylsulfonyl)piperidin-4-yl]methyl}-6-fluorobenzamide | 417.1 |
| | 2-chloro-N-{[4-(cyclopropylmethyl)-1-[(2,2,2-trifluoroethyl)sulfonyl]piperidin-4-yl}methyl)-4-fluorobenzamide | 471.1 |
| | N-{[4-(cyclopropylmethyl)-1-(ethylsulfonyl)piperidin-4-yl]methyl}cyclohexanecarboxamide | 371.2 |
| | N-{[4-(cyclopropylmethyl)-1-(ethylsulfonyl)piperidin-4-yl]methyl}-2-(trifluoromethyl)benzamide | 433.1 |

TABLE 1-continued

| Compound | Nomenclature | MS M + 1 |
|---|---|---|
| | N-{[4-(cyclopropylmethyl)-1-(ethylsulfonyl)piperidin-4-yl]methyl}-2,4-difluorobenzamide | 401.1 |
| | N-{[4-(cyclopropylmethyl)-1-(ethylsulfonyl)piperidin-4-yl]methyl}-2,6-difluorobenzamide | 401.1 |
| | 2-chloro-N-{[4-(cyclopropylmethyl)-1-(ethylsulfonyl)piperidin-4-yl]methyl}-4,6-difluorobenzamide | 435.1 |
| | N-{[4-(cyclopropylmethyl)-1-(ethylsulfonyl)piperidin-4-yl]methyl}-2,3-difluorobenzamide | 401.1 |

TABLE 1-continued

| Compound | Nomenclature | MS M + 1 |
|---|---|---|
|  | 2,4-dichloro-N-{[4-(cyclopropylmethyl)-1-(propylsulfonyl)piperidin-4-yl]methyl}benzamide | 447.1 |
|  | N-{[4-(cyclopropylmethyl)-1-(propylsulfonyl)piperidin-4-yl]methyl}-2-furamide | 369.1 |
|  | 2-chloro-N-{[4-(cyclopropylmethyl)-1-(isopropylsulfonyl)piperidin-4-yl]methyl}-4-fluorobenzamide | 431.1 |
|  | 2,4-dichloro-N-{[4-(cyclopropylmethyl)-1-(cyclopropylsulfonyl)piperidin-4-yl]methyl}benzamide | 445.1 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of Formula I

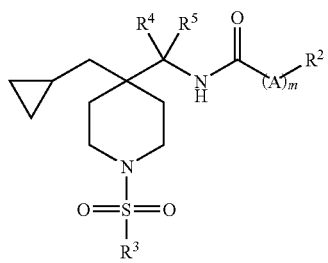

wherein $R^2$ is selected from the group consisting of:
  (1) phenyl, which is substituted with $R^{2a}$, $R^{2b}$ and $R^{2c}$,
  (2) furanyl, which is substituted with $R^{2a}$, $R^{2b}$ and $R^{2c}$,
  (3) cyclohexyl, which is unsubstituted or substituted with 1-6 halogen, hydroxy or —$NH_2$,
$R^{2a}$, $R^{2b}$ and $R^{2c}$ are independently selected from the group consisting of:
  (1) hydrogen,
  (2) halogen,
  (3) —$C_{1-6}$alkyl,
  (4) —$CF_3$, and
  (5) —$NH_2$;
$R^3$ is $C_{1-6}$alkyl or cyclopropyl;
$R^4$ and $R^5$ are independently selected from the group consisting of:
  (1) hydrogen, and
  (2) $C_{1-6}$alkyl, which is unsubstituted or substituted with halogen or hydroxyl, or $R^4$ and $R^5$ taken together form a $C_{3-6}$cycloalkyl ring;
A is selected from the group consisting of:
  (1) —O—, and
  (2) —NH—;
m is zero, whereby $R^2$ is attached directly to the carbonyl;
or a pharmaceutically acceptable salt thereof.

2. The compound of claim 1 of the formula Id':

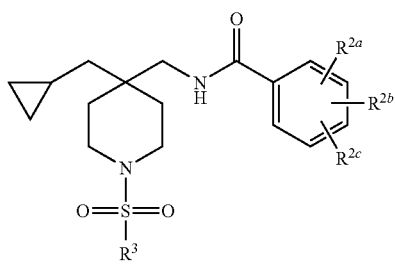

or a pharmaceutically acceptable salt thereof.

3. The compound of claim 1 wherein $R^2$ is phenyl or furanyl and $R^{2a}$, $R^{2b}$ and $R^{2c}$ are independently selected from the group consisting of:
  (1) hydrogen,
  (2) halogen,
  (3) —$C_{1-6}$alkyl,
  (4) —$CH_3$, and
  (5) —$NH_2$.

4. The compound of claim 3 wherein $R^2$ is phenyl and $R^{2a}$, $R^{2b}$ and $R^{2c}$ are independently selected from the group consisting of:
  (1) hydrogen,
  (2) fluoro,
  (3) chloro,
  (4) bromo,
  (5) —$CH_3$, and
  (6) —$NH_2$.

5. The compound of claim 4 wherein $R^2$ is selected from the group consisting of:
  (1) 2,3-difluorophenyl,
  (2) 2,4-difluorophenyl,
  (3) 2,4-dichlorophenyl,
  (4) 2-chloro-4-fluorophenyl,
  (5) 2-chloro-6-fluorophenyl, and
  (6) 2-chloro-4,6-difluorophenyl.

6. The compound of claim 1 wherein $R^3$ is $C_{1-6}$alkyl.

7. The compound of claim 6 wherein $R^3$ is —$CH_2CH_3$.

8. The compound of claim 6 wherein $R^3$ is cyclopropyl.

9. The compound of claim 1 wherein $R^4$ is hydrogen and $R^5$ is hydrogen.

10. A compound which is selected from the group consisting of:

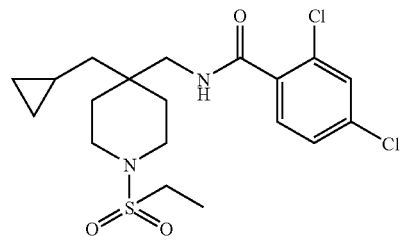

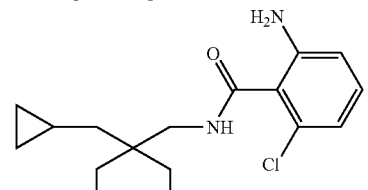

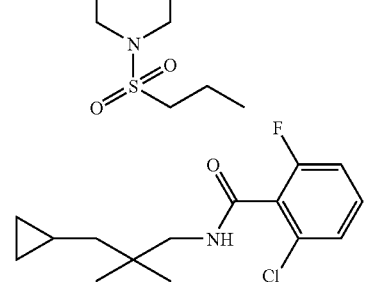

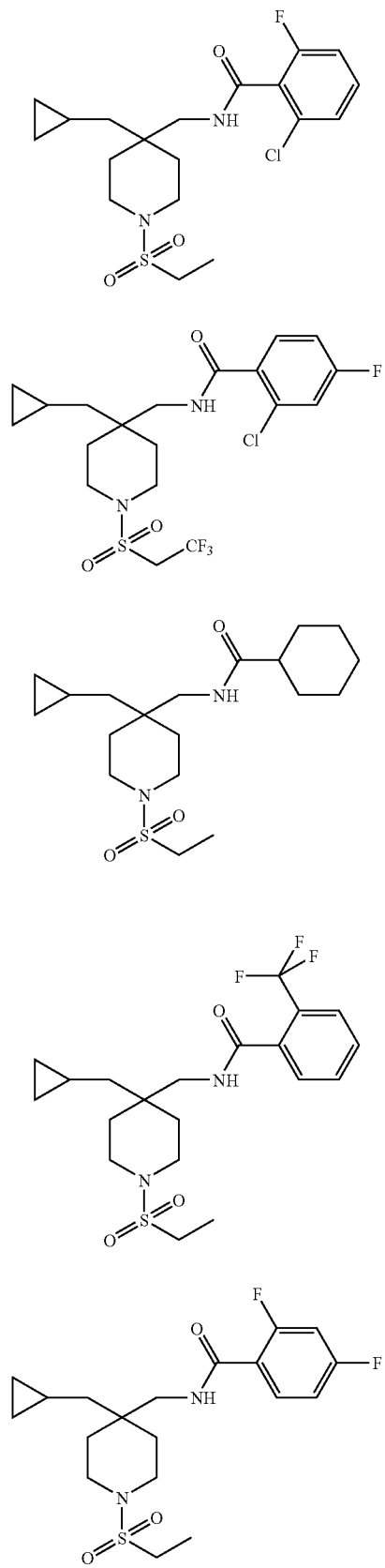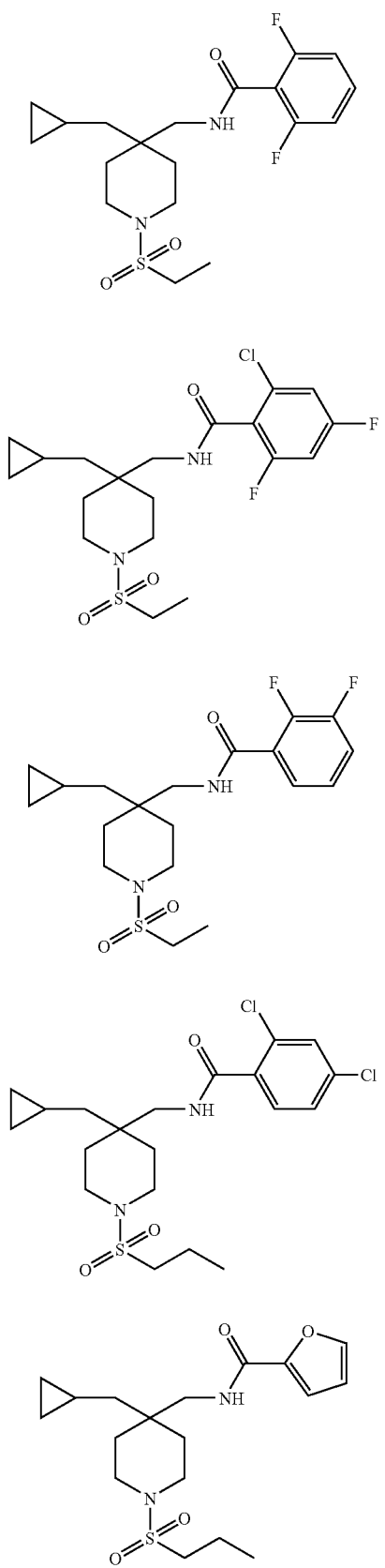

-continued

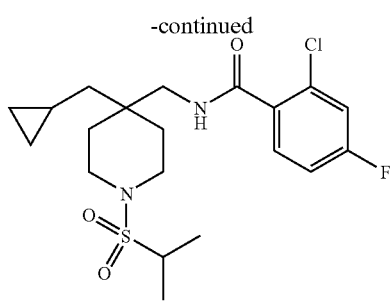

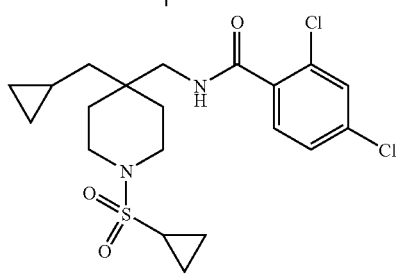

or a pharmaceutically acceptable salt thereof.

11. A compound which is:

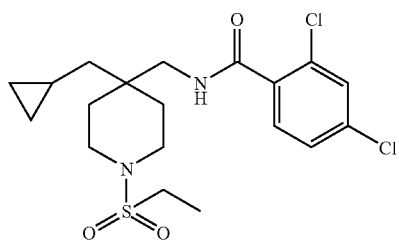

or a pharmaceutically acceptable salt thereof.

12. A pharmaceutical composition which comprises a pharmaceutically acceptable carrier and the compound of claim 1 or a pharmaceutically acceptable salt thereof.

13. A pharmaceutical composition which comprises a pharmaceutically acceptable carrier and the compound of claim 11 or a pharmaceutically acceptable salt thereof.

* * * * *